US007556830B2

(12) United States Patent
Chepkwony et al.

(10) Patent No.: US 7,556,830 B2
(45) Date of Patent: Jul. 7, 2009

(54) MEDICINAL HERBAL COMPOSITION FOR TREATING INFECTION

(75) Inventors: Paul Kiprono Chepkwony, Eldoret (KE); Maria Medina, Nairobi (KE); Mitchell Medina, Nairobi (KE)

(73) Assignee: International Patents Holdings, Ltd., Hamilton (BM)

( * ) Notice: Subject to any disclaimer, the term of this patent is extended or adjusted under 35 U.S.C. 154(b) by 0 days.

(21) Appl. No.: 11/352,931

(22) Filed: Feb. 13, 2006

(65) Prior Publication Data

US 2007/0042053 A1    Feb. 22, 2007

Related U.S. Application Data

(60) Provisional application No. 60/710,237, filed on Aug. 22, 2005.

(51) Int. Cl.
   *A61K 36/00*    (2006.01)
(52) U.S. Cl. .................................................. 424/725
(58) Field of Classification Search ................... None
See application file for complete search history.

(56) References Cited

U.S. PATENT DOCUMENTS

| | | | |
|---|---|---|---|
| 5,178,865 A | 1/1993 | Ho et al. | |
| 5,366,725 A | 11/1994 | Okubo et al. | |
| 5,411,733 A | 5/1995 | Hozumi et al. | |
| 5,837,257 A | 11/1998 | Tsai et al. | |
| 5,989,556 A | 11/1999 | Tsai et al. | |
| 6,455,078 B1 | 9/2002 | Wu | |
| 6,696,094 B2 | 2/2004 | Wu | |

OTHER PUBLICATIONS

Broutin et al.; Whooping Cough Metapopulation Dynamics.; Proc. R. Lond. B(Suppl.); 271; 2004.; pp. S302-S305.*
Asres, et al., Antiviral Activity Against Human Immunodeficiency Virus Type 1 (HIV-1) and Type 2 (HIV-2) of Ethnobotanically Selected Ethiopian Medicinal Plants, *Phytother. Res.*, 15, 62-69 (2001).
Chang, et al., Differential inhibition of reverse transcriptase and cellular DNA polymerase-α activities by lignans isolated from Chinese herbs, *Phyllanthus myrtifolius* Moon, and tannins from *Lonicera japonica* Thunb and *Castanopsis hystrix*, Antiviral Research, 27 (4), 367-374 (1995).
Cos, et al., Antiviral activity of Rwandan medicinal plants against human immunodeficiency virus type-1 (HIV-1), *Phytomedicine*, 9, 62-68 (2002).
Houghton, et al., A Clinical Evaluation of the Chinese Herbal Mixture 'Aden-I' for Treating Respiratory Infections, *Phytother. Res.*, 7(5), 384-386 (1993).
John, et al., Synergistic Antiretroviral Activities of the Herb, *Prunella vulgaris*, with AZT, ddI, and ddc, Abstr. Gen. Meet. Am. Sc. Microbiol., 94, 481 (1994).
Kane, et al., Methyl Gallate, Methyl-3, 4, 5-trihydroxy-benzoate, is a Potent and Highly Specific Inhibitor of Herpes Simplex Virus in vitro. I. Purificaton and Characterization of Methyl Gallate From *Sapium sebiferum*, Bioscience Report, 8, 85-94 (1988).
Kuritzkes, Laboratory Tests for Monitoring HIV-1 Infection, HIV and Hepatitis.com, p. 1-24, (2001).
Nagai, et al., Inhibition of Influenza Virus Sialidase and Anti-influenza Virus Activity by Plant Flavonoids, *Chem. Pharm Bull*. 38(5), 1329-1332 (1990).
Tabba, et al Tabba, et al., Isolation, purification, and partial characterization of prunellin, an anti-HIV component from aqueous extracts of *Prunella vulgaris*, Antiviral Research, 11, 263-273 (1989).
Takechi and Tanaka, Purification and Characterization of Antiviral Substance from the Bud of *Syzygium aromatica*, Planta Medica, 42, 69-74 (1981).
Vecchiato, Sociocultural Aspects of Tuberculosis Control in Ethiopia, Medical Anthropology Quarterly, 11(2):183-201 (1997).
Yamasaki, et al., Screening Test of Crude Drug Extract on Anti-HIV Activity, Yakugaku Zasshi, 113(11), 818-824 (1993).
Yao, et al., Mechanism of Inhibition of HIV-1 Infection in vitro by Purified Extract of *Prunella vulgaris*, Virology, 187(1), 56-62 (1992).
Baldascini, "Income generating opportunities arising from natural exosystems in Uganda: an overview", The International Food Policy Research Institute, (2002) pp. 1-39.
Cos et al., "Further evaluation of Rwandan medicinal plant extracts for their antimicrobial and antiviral activities", Journal of Ethnopharmacology (2002) 79:155-163. Abstract Only.
Cui et al., "Clinical efficacy of compound periploca liquid in treating condyloma acuminatum and its effect on human papilloma virus DNA expression in vitro", Zhongguo Zhong Xi Yi Jie He Za Zhi (2005) 25:392-6. Abstract Only.
DeBoer et al., "Anti-fungal and anti-bacterial activity of some herbal remedies from Tanzania", Journal of Ethnopharmacology (2005) Available online Nov. 11, 2004, vol. 96, p. 461469. Abstract.
Eloff, "Which extractant should be used for the screening and isolation of antimicrobial components from plants?" Journal of Ethnopharmacology (1998) 60:1-8. Abstract only.
Geyid et al., "Screening of some medicinal plants of Ethiopia for their anti-microbial properties and chemical profiles", J. Ethnopharmacol (2005) 97:421-427. Abstract only.
Giday, "An ethnobotanical study of medicinal plants used by the Zay people in Ethiopia", CBMs: s Skriftseria (2001) 1:81-99.

(Continued)

*Primary Examiner*—Patricia Leith
*Assistant Examiner*—Melenie McCormick
(74) *Attorney, Agent, or Firm*—Cooper & Dunham LLP

(57) ABSTRACT

Herbal compositions derived from Kenyan plants are provided for the treatment of HIV and other infectious diseases. The herbal compositions can include the extracts of up to 14 plants, including the root of *abyssinica* and *Clutia robusta*. Also provided are methods for extracting alkaloids and other compounds from the plants. Also provided are methods of treating a subject having an infectious disease, particularly HIV.

14 Claims, 1 Drawing Sheet

OTHER PUBLICATIONS

Kraft et al., In vitro antiplasmodial evaluation of medicinal plants from Zimbabwe Phytotherapy Research (2003) 17:123-128. Abstract only.

Mulholland et al., "The Chemistry of the Meliaceae and Ptaeroxylaceae of Southern and Eastern Africa and Madagascar" Current Organic Chemistry (2002) 4:1011-1054.

Verschaeve et al., "Investigation of the antimutagenic effects of selected South African medicinal plant extracts", Toxicology in Vitro (2004) 18:29-35. Abstract Only.

Yamada, "A Report on the Ethnobotany of the Nyindu in the Eastern Part of the Former Zaire", African Study Monographs (1999) 20:1-72.

* cited by examiner

Relationship of CD4 Count to development of opportunistic infections.

MEDICINAL HERBAL COMPOSITION FOR TREATING INFECTION

FIELD OF THE INVENTION

The present invention relates to combinations of extracts from plants that can be used in the treatment of infection.

BACKGROUND OF THE INVENTION

This application claims the benefit of provisional application Ser. No. 60/710,237, filed Aug. 22, 2005, incorporated herein by reference in its entirety. The following discussion of the background of the invention is merely provided to aid the reader in understanding the invention and is not admitted to describe or constitute prior art to the present invention.

Tens of millions of people world-wide are living with acquired immunodeficiency syndrome (AIDS), or are infected with the causative agent, human immunodeficiency virus (HIV). In some countries in sub-Saharan Africa, up to one in four adults has contracted the disease. Despite the costs and efforts spent attempting to identify new methods of treatment, a cure for the disease has remained elusive.

Ancient societies have traditionally turned to plants for their health needs. Documented use of herbs to treat illnesses dates back to as early as 2,000 B.C. Recently, individuals have resorted to nature as remedies and medicines for the treatment of modern illnesses have been derived from plants, such as for example, treatment of HIV and other infectious diseases.

For example, U.S. Pat. No. 5,178,865 discloses an experimental treatment with 56 herbs, and reports that 10 of the 56 herbs exhibit anti-HIV activity in in vitro experiments. The 10 herbs include: *Coptis chineusis, Ligusticum wallichii, Ilicium eanclolatum, Isatis tinctoria, Salvia miltiorrhiza, Erycibe obtusifolia, Acanthopanax graciliatylus, Bostaurus domesticus, Inula helenium* and *Lonicera japonica*. Both *Bostaurus domesticus* and *Lonicera japonica* are further described to be able to combine with *Scutellaria baicaleusis* to exhibit anti-HIV activity.

U.S. Pat. No. 5,837,257 discloses Chinese herbal medicines that exhibit in vitro antiviral activity against murine leukemia virus and HIV and for treatment of animals and humans infected with HIV. In one of the preferred embodiments, the Chinese herbal medicines contain hedyotis, *Scutellarial barbatae herba, Lonicera flos, Prunellae spica* and *Solani harba*.

U.S. Pat. No. 5,989,556 discloses various herbal compositions for treating viral infections which have shown in vitro antiviral activities against HIV. A first herbal composition contains *Aeginetiae herba, Blechni rhizoma, Lespedezae herba, Polygoni cuspidati rhizoma, Forsythiae fructus,* and *Ligustri fructus*. A second herbal composition contains *Cirsii rhizoma* and radix, *Breeae radix, Baphicacanthis rhizoma* and radix, *Phellodendri* cortex, and *Bletillae* tuber. A third herbal composition disclosed in the patent includes *Aeginetiae Herba, Lonicerae, Flos, Prunellae spica* and *Lespedezal herba*.

U.S. Pat. No. 6,696,094 discloses an herbal pharmaceutical composition for treating HIV/AIDS. The pharmaceutical composition contains 14 ingredients, including: diffuse hedyotis, bistort rhizome, giant knotweed rhizome, Asiatic moonseed rhizome, baical skullcap root, Bovine biliary powder, milkvetch root, barbary wolfberry fruit, sanqi, figwort root, Chinese magnoliavine fruit, turmeric root-tuber, hawthorn fruit and Chinese angelica. Procedures are provided for the preparation of an "HIVCIDE condensate", which can be formulated as an injectible solution or as capsules. Results indicate that subjects injected with HIVCIDE solution showed no symptoms of acute or chronic toxicity. Further, the HIVCIDE injection solution was effective in inhibiting pathological changes in cells caused by HIV-1 in vitro. In a third experiment, the HIVCIDE injection solution was effective in reducing symptoms of HIV-infected subjects in a treatment regime together with administration of HIVCIDE capsules. HIV-positive subjects did not show adverse reactions to HIVCIDE injection solution. It was further reported three out of four subjects showed improvement in fatigue after treatment with HIVCIDE, and that HIV viral load studies indicated that all subjects demonstrated reduced HIV viral loads.

U.S. Pat. No. 6,455,078 discloses a medical herbal composition for treating liver diseases and HIV. The composition contains 15 ingredients, which includes diffuse hedyotis, bistort rhizome giant knotweed rhizome, Asiatic moonseed rhizome, baical skullcap root, bovine biliary powder, milkvetch root, barbary wolfberry fruit, sanqi, red gingseng, figwort root, Chinese magnoliavine fruit, turmeric root-tuber, hawthorn fruit and Chinese angelica. Among the 15 ingredients, diffuse hedyotis, bistort rhizome, giant knotweed rhizome, and Chinese magnoliavine fruit are cited as being necessary to contribute to the efficacy of the pharmaceutical composition.

In U.S. Pat. No. 5,366,725, an extract from the seeds of *Aeginetia indica* was prepared which exhibited excellent carcinostatic effects and possesses interleukin-2 and interferon-gamma-inducing properties. The extract is believed to be a macromolecular polysaccharide, which may or may not contain Lipid A binding with protein depending on whether the extraction is conducted using butanol or phenol. The extracted substance is soluble in water, insoluble in n-butanol, and has a molecular weight ranging from 100,000 to 200,000 Daltons.

U.S. Pat. No. 5,411,733 to Hozumi, et al., discloses a variety of plant extracts for use as anti-herpes viral, anti-polioviral, anti-varicella-zoster virus, anti-measles virus, anti-cytomegalovirus (CMV), and anti-DNA and anti-RNA virus agents.

U.S. Pat. No. 5,178,865 discloses the anti-HIV activity in vitro of a variety of herbs known in China to exhibit anti-viral activity. Water extractions of the mixtures, treatment with ethanol for precipitation and charcoal adsorption are disclosed for the preparation for the anti-HIV-active composition.

Two lignans, phyllamycin B and retrojusticiden B, have been reported to have an inhibitory effect on HIV-1 reverse transcriptase activity. The lignans are isolated from *Phyllanthus myrtifolius* Moon, a plant widely grown in Southern China. See, for example, Chang, et al., *Antiviral Research*, 27 (4), 367-374 (1995).

A mixture of aqueous extracts of *Lonicera japonica* flower buds, *Forsythia suspensa* fruits, and *Scutellaria baicalensis* rootbark have been shown to have antibacterial and antiviral properties. Subjects with severe respiratory disease treated with the mixture responded as well as a control group on standard antibiotic therapy. See Houghton, et al., *Phytother. Res.*, 7(5), 384-386 (1993).

A water extract of *Prunella vulgaris* was reported to have anti-HIVB activity when administered in combination with zidovudine (AZT) and didanosine (dd1). Only a slight additive effect was observed for the administration of an extract of *Prunella vulgaris* and zalcitabine (ddC). See John, et al., Abstr. Gen. Meet. Am. Sc. Microbiol., 94, 481 (1994).

Yamasaki et al. have reported the in vitro evaluation of 204 crude drugs commonly used in Japan for anti-HIV-1 activity and studies indicate that hot water extracts of *Lithospermum*

*erythrorhizon* (root) and *Prunella vulgaris* (spike) showed strong in vitro anti HIV-1 activity with an $IC_{100}$ of 16 µg/mL. See Yamasaki, et al., *Yakugaku Zasshi*, 113(11), 818-824 (1993).

Yao et al. have reported that water extracts of dried *Prunella vulgaris* (whole plant) were active in vitro for inhibiting HIV-1 replication, and showed relatively low cytotoxicity to MT-4 cells. The extract also demonstrated activity in the inhibition of reverse transcriptase. The active factor was purified and identified as anionic with a molecular weight of approximately 10,000 Daltons. This active component may be the same as the prunellin, as described by Tabba, et al., (1989). The purified extract inhibited HIV-1 replication in the lymphoid cell line MT-4, in the monocytoid cell line U937, and in peripheral blood mononuclear cells (PBMC) at effective concentrations of 6.3 and 12.5 µg/mL, respectively. Pretreatment of uninfected cells with the extract prior to viral exposure did not prevent HIV-1 infection upon subsequent exposure to the virus. Preincubation with the purified extract decreased HIV-1 infectiousness. The purified extract also blocked cell-to-cell transmission of HIV-1, prevented syncytium formation, and interfered with the ability of both HIV-1 and purified gp 120 to bind to CD4. PCR (polymerase chain reaction) analysis confirmed the absence of HIV-1 proviral DNA in cells exposed to virus in the presence of the extract, suggesting that the purified extract antagonized HIV-1 infection of susceptible cells by preventing viral attachment to the CD4 receptor. See Yao, et al., *Virology*, 187(1), 56-62 (1992).

Tabba, et al. isolated and partially characterized prunellin, a compound exhibiting anti-HIV properties, from aqueous extracts of *Prunella vulgaris*, a Chinese herb. Prunellin was identified as a carbohydrate (a partially sulfated polysaccharide) with an minimum inhibition concentration of 2.2 µg/mL against HIV-1 in vitro. It was identified as having a molecular weight of about 10,000 Dalton. See Tabba, et al., *Antiviral Research*, 11, 263-273 (1989).

Antiviral agents have been isolated from *Syzygium aromatica*, *Sapium sebiferum* (Chinese tallow tree leaves), *Scutellaria baicalensis*, and *Scutellaria rivularis*. Eugeniin, (a tannin isolated from *Syzygium aromatica*), and methyl gallate, (isolated from *Sapium sebiferum*), exhibited anti-herpes simplex virus (HSV-2) activity in vitro. Plant flavonoids, such as 5,7,4-truhydroxyflavone, extracted from the whole herb *Scutellaria rivularis*, were reported to have anti-influenza virus activity. See Hozumi, et al., U.S. Pat. No. 5,411,733; Takechi, et al., *Planta Medica*, 42, 69-74 (1981); Kane, et al., *Bioscience Report*, 8, 85-94 (1988); and Nagai, et al., *Chem. Pharm Bull.* 38(5), 1329-1332 (1990).

Ethiopian medicinal plants known for treatment of a variety of ailments were screened for activity against HIV-1 and HIV-2, as reported by Asres, et al. Extracts from *Bersama abyssinica* root bark, *Combretum paniculatum* leaves, *Dodonaea angustfolia* leaves, and *Ximenia Americana* stem bark each displayed anti-viral activity at concentrations that were non-toxic to MT-4 cells. Anti-viral activity of the extracts is noted to be more effective against HIV-1 than HIV-2. See Asres, et al., *Phytother. Res.*, 15, 62-69 (2001).

Selected plants used in traditional Rwandan medicine for treatment of infections and/or rheumatoid diseases were investigated for antiviral activity in vitro against HIV-1. See Cos, et al., *Phytomedicine* 9, 62-68 (2002). Of 38 plant extracts tested, extracts from the leaves of *Aspilia pluriseta* and *Rumex bequaertii* had the highest antiviral activities.

SUMMARY OF THE INVENTION

The present invention is based upon the discovery of the unique antiviral properties of a herbal remedy composition prepared from a variety of plants native to Kenya. The herbal composition of the present invention can include plant material from between two and 14 different plants preferably including roots of *abyssinica* (representative seed of said line having been deposited under ATCC Accession No. PTA-6769) and *Clutia robusta* (representative seed of said line having been deposited under ATCC Accession No. PTA-6970). For treatment of infectious disease, the herbal composition of plant material may be extracted to produce a liquid herbal composition or further purified to obtain alkaloid compounds from the plant material. The liquid herbal composition prepared from aqueous extracts from the plants has demonstrated effectiveness in treating HIV-positive subjects, as subjects treated with the liquid herbal composition have experienced improvements in CD4+ cell counts, and in some cases, complete reversal of HIV positive status.

In one aspect, the invention provides a herbal composition for treating infectious diseases, such as for example, HIV. The composition containing plant material includes the roots of *abyssinica* and the roots of *Clutia robusta*. In other embodiments of the invention, the herbal pharmaceutical composition may also include plant material, as indicated, from one or more of the following: stem bark of *Prunus africana* stem bark of *Croton macrostachyus*, stem bark of *Acacia nilotica* (representative seed of said line having been deposited under ATCC Accession No. PTA-7378), roots of *Rhamnus prinoides*, roots of *Adenia gummifera*, roots of *Asparagus africanus*, stem bark of *Anthocleista grandiflora*, whole plant of *Plantago palmata* (representative seed of said line having been deposited under ATCC Accession No. PTA-7377), roots of *Clematis hirsuta*, stem bark of *Ekebergia capensis*, stem bark of *Bersama abyssinica*, and roots of *Periploca linearifolia*.

In another aspect, the invention provides a method for preparing a liquid extract of the solid herbal composition of the invention. The extraction of plant material can be done with hot water. In one embodiment, hot aqueous extraction is done under basic conditions, followed by hot aqueous extraction under acidic conditions. In further embodiments, desired alkaloid compounds purified from the liquid extracts are provided or produced from direct chemical synthesis.

The invention further provides aqueous extracts of the herbal compositions of the invention. Also provided are alkaloid compounds purified from aqueous extracts and the chemical synthesis of the herbal compositions of the invention.

In another aspect of the present invention a method for treating HIV-positive subjects is provided. Subjects are administered an effective amount of a herbal composition of the invention prepared from the aqueous extracts of *Dovyalis abyssinica* and *Clutia robusta*, alone or in combination with one or more of the following: *Prunus africana, Croton macrostachyus, Acacia nilotica, Rhamnus prinoides, Adenia gummifera, Asparagus africanus, Anthocleista grandiflora, Plantago palmata, Clematis hirsuta, Ekebergia capensis, Bersama abyssinica*, and *Periploca linearifolia*, in doses based on subjects' body weights. In other embodiments the herbal composition of the invention is prepared from purified alkaloid compounds obtained from the aqueous extracts. The herbal compositions are administered at least once a day. In other embodiments, the herbal composition is administered twice or three times daily, based upon the health of the subject. In other embodiments, the composition may be administered as a beverage, capsule, tablet, powder, candy, gel, nutritional product or pharmaceutical product.

In another aspect of the present invention provides an herbal composition for treating subjects having infection, such as for example, HIV or AIDS. The herbal composition consists essentially of extracts of *abyssinica* and *Clutia robusta*, and optionally one or more of the following: *Prunus africana, Croton macrostachyus, Acacia nilotica, Rhamnus prinoides, Adenia gummifera, Asparagus africanus, Anthocleista grandiflora, Plantago palmata, Clematis hirsuta, Ekebergia capensis, Bersama abyssinica*, and *Periploca linearifolia*. In one embodiment, the herbal composition of the invention is prepared from purified alkaloid compounds obtained from aqueous extracts.

In another aspect of the present invention a method is provided for treating subjects having infection, such as for example, HIV or AIDS. Subjects are administered an effective amount of a herbal composition consisting essentially of extracts of *abyssinica* and *Clutia robusta*, and optionally the extract of one or more of the following: *Prunus africana, Croton macrostachyus, Acacia nilotica, Rhamnus prinoides, Adenia gummifera, Asparagus africanus, Anthocleista grandiflora, Plantago palmata, Clematis hirsuta, Ekebergia capensis, Bersama abyssinica*, and *Periploca linearifolia*, in doses based on subjects' body weights. In other embodiments the herbal composition of the invention is prepared from purified alkaloid compounds obtained from the aqueous extracts. The herbal compositions can be administered at least once a day. In other embodiments, the herbal composition can be administered twice or three times daily, based upon the health of the subject. In other embodiments, the composition may be administered as a beverage, capsule, tablet, powder, candy, gel, nutritional product or pharmaceutical product.

As used herein, a person is considered HIV-negative if he/she has tested negative on the two-part HIV screening test (ELISA and Western blot).

As used herein, the term "therapeutically effective" or "effective amount" indicates that the materials or amount of material is effective to prevent, alleviate, or ameliorate one or more symptoms of a disease or medical condition, and/or to prolong the survival of the subject being treated.

As used herein, "pharmaceutically acceptable" indicates that the identified material does not have properties that would cause a reasonably prudent medical practitioner to avoid administration of the material to a subject, taking into consideration the disease or conditions to be treated and the respective route of administration.

As used herein, the term "composition" refers to a formulation suitable for administration to an intended animal subject for therapeutic purposes that contains at least one pharmaceutically active compound and at least one pharmaceutically acceptable carrier or excipient.

"About" is used herein to mean in quantitative terms plus or minus 10%.

As used herein, amelioration of the symptoms of a particular disorder by administration of a particular pharmaceutical composition refers to any lessening, whether permanent or temporary, lasting or transient that can be attributed to or associated with administration of the composition.

As used herein, "combination" refers to any association between or among two or more items. The combination can be two or more separate items, such as two compositions or two collections. It can be a mixture thereof, such as a single mixture of the two or more items, or any variation thereof.

As used herein, "composition" refers to any mixture. It can be a solution, a suspension, liquid, powder, a paste, aqueous, non-aqueous or any combination thereof.

As used herein, "ingredient of a pharmaceutical composition" refers to one or more materials used in the manufacture of a pharmaceutical composition. Ingredient can refer to an active ingredient (an agent) or to other materials in the compositions. Ingredients can include water and other solvents, salts, buffers, surfactants, water, non-aqueous solvents, and flavorings.

As used herein, "pharmaceutical composition" refers a composition that contains an agent and one or more other ingredients that is formulated for administration to a subject. An agent refers to an active ingredient of a pharmaceutical composition. Typically active ingredients are active for treatment of a disease or condition. For example, agents that can be included in pharmaceutical compositions include agents for treating infectious disease.

As used herein, "treatment" refers any manner in which the symptoms of a condition, disorder or disease or other indication, are ameliorated or otherwise beneficially altered.

As used herein, "extraction" refers to a method of separation in which a solid or solution is contacted with a liquid solvent to transfer one or more components of the solid into the solvent.

As used herein, an extract refers to a solution containing compound(s), usually in a concentrated form, obtained by treating a solid material (such as for example, plant material) with a solvent to remove desired compounds or components.

As used herein, "synthesized alkaloid compounds" refers alkaloid compounds obtained by chemical synthesis.

As used herein, "CD4+ T cell" (or "T helper cell") refers to an immune T cell which is involved in protecting against infectious agents including viral, fungal and protozoal infectious agents. The CD4 molecule is expressed on the surface of T helper cells, which also serves as the primary target for HIV-1 and HIV-2. CD4 is the co-receptor for the T cell receptor and recruits the tyrosine kinase 1 ck intracellularly. CD4+ cell counts are reduced with the progression of HIV.

As used herein, "CD8+ T cell" refers to an immune T cell which has cytotoxic activity for infected cells. The CD8 molecule is expressed on the surface of T cytoxic lymphocytes. CD8 T-lymphocyte counts increase at the onset of HIV infection and continue to rise through the progression of the disease.

As used herein, "CD4+/CD8+ ratio" refers to the ratio of CD4+ cells to CD8+ cells in a given sample, and is an important measure of disease progression.

As used herein, "cluster of differentiation" (CD) molecules are markers on the cell surface, as recognized by specific sets of antibodies, used to identify the cell type, stage of differentiation and activity of a cell.

As used herein, the terms "HIV" and "AIDS-related virus" mean the commonly designated HIV series (human immunodeficiency virus) and species thereof.

As used herein, the terms "HIV-related disease" and "AIDS-related disease" shall refer to any illness or syndrome, caused directly or indirectly by HIV or AIDS-related virus, including but not limited to infections whose source is fungal, viral and/or bacterial.

As used herein, "highly active antiretroviral therapy", or HAART, refers to treatment regimens designed to aggressively suppress viral replication and progress of HIV disease, usually consisting of three or more different drugs, such as for example, two nucleoside reverse transcriptase inhibitors and a protease inhibitors.

As used herein, "acute HIV infection" refers to the period of rapid viral replication immediately following exposure to HIV.

As used herein, "AIDS wasting syndrome" refers to the involuntary weight loss of 10 percent of baseline body weight plus either chronic diarrhea or chronic weakness and documented fever in the absence of a concurrent illness or condition other than HIV infection.

As used herein, "antiviral" refers to a substance or process that destroys a virus or suppresses replication (reproduction) of the virus.

As used herein, "viral load test" (in relation to HIV) refers to a test that measures the quantity of HIV RNA in the blood, expressed as number of copies per mL of blood plasma.

DETAILED DESCRIPTION OF THE INVENTION

Figure 1:
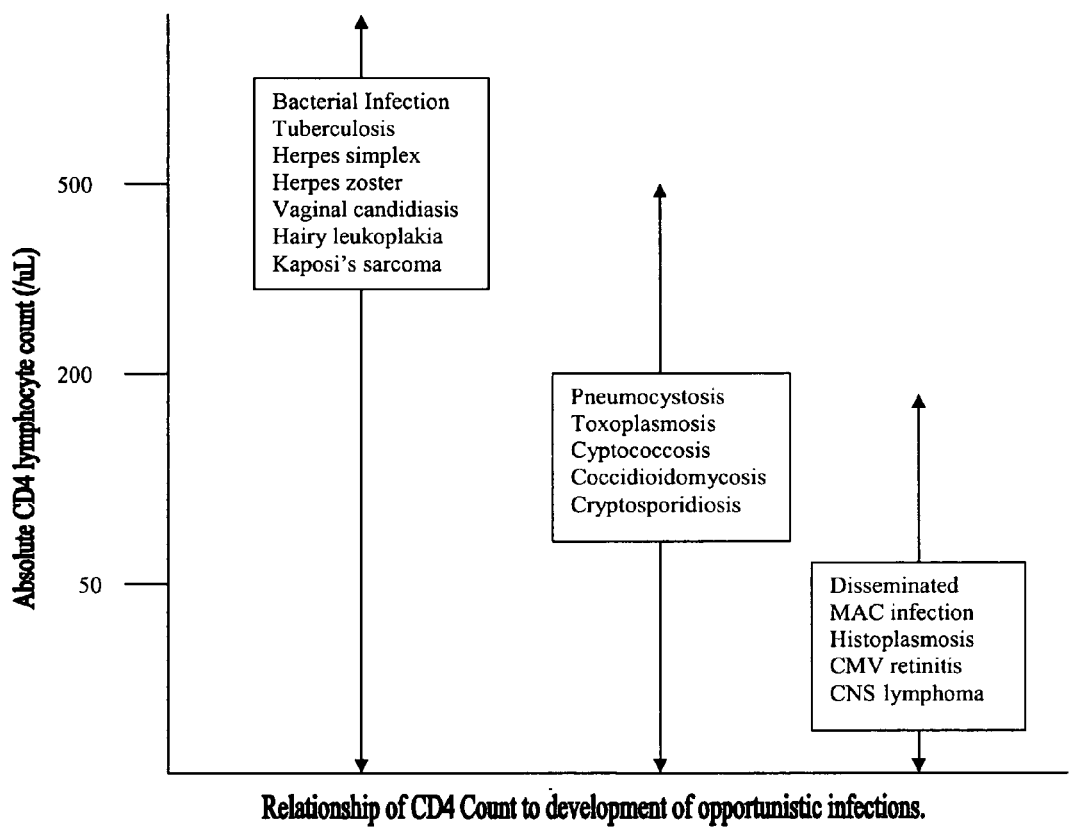
FIG. 1 shows relationships between observed clinical symptomatology and CD4+ count results.

The present invention relates to the discovery that combinations of extracts from plants native to Kenya can be used in the treatment of infection, such as for example, HIV and AIDS. Herbal compositions prepared from combinations of the extracts of the following: the roots of *abyssinica* and *Clutia robusta, Rhamnus prinoides, Adenia gummifera, Asparagus africanus, Clematis hirsuta,* and *Periploca linearifolia*, the stem bark of *Ekebergia capensis, Bersama abyssinica, Prunus africana, Croton macrostachyus, Acacia nilotica,* and *Anthocleista grandiflora*, and the whole plant of *Plantago palmata* have been shown to be particularly effective in improving the health of infected subjects. Specifically, herbal compositions of the present invention are particularly well suited for the treatment of infectious diseases including HIV.

Compositions of the invention can be prepared from plant material collected from the Mau Forest Complex in Western Kenya. Herbal compositions prepared from aqueous extractions and purified extracts of plants from this region of Kenya exhibit increased potency in the treatment of infectious diseases. The Mau Forest Complex is located at 0° 30' South, 35° 20' East and in the Rift Valley Province, and spans four Kenyan administrative districts: Narok, Nakuru, Bomet and Kericho. Mean annual rainfall varies from 1000 to 1500 mm with peaks in April and August. The rainfall pattern at the western flanks is governed by the moist monsoon winds from the Indian Ocean and dry winds from the Great Rift Valley. The western flanks of the Mau Forest Complex are influenced by the Lake Victoria macroclimatic region and are generally wetter with annual rainfall greater than 2000 mm and more evenly distributed. Mean annual temperatures for the Mau Forest Complex range from 12-16° C. The soil of the Mau Forest Complex is rich volcanic loam having a pH between 3.8-5.8.

The vegetational pattern follows an altitudinal gradient with local topographical ecolines. The closed canopy moist mountain forest at lower altitudes becomes increasingly intermixed with bamboo from 2200 m onwards. Between 2300 and 2500 m, pure bamboo (*Arundinaria alpina*) swards are found. Above 2500 m this gives way to mixed bamboo/tree stands, both associated with grass clearings that usually represent a sub-climax resulting from burning and cutting of bamboo. A marginal type of mountain sclerophyll forest, wherein the plants generally have hard leaves to prevent wilting during dry conditions, occupies the highest altitudes of the Mau complex.

Plants in the Western flank of the Mau Forest Complex have shown the highest potency for the herbal compositions. Plants growing in the Western flank, (which is generally a high rainfall, high altitude region), have fewer environmental stresses. It is therefore possible that plants of the Western flank have more biosynthetic pathways, which may in turn lead to the production of a greater number of diverse compounds, which may in turn explain the greater potency of plants from the Western flank (as compared to other regions of the Mau Forest Complex). Alternatively, the greater potency plant extracts from the Western flank plants may be a result of a greater variety and number of alkaloids and other compounds in the plant extracts, such that the combined effect is greater than the sum of their individual effects.

The East Mau Forest Complex has a drier vegetation of Cedar and Podo. Wherever these species have been extracted, colonizing species such as *Neuboutonia marcrocalyx* and *Macaranga capensis* can be found.

The compositions of the invention may be prepared using plants collected from three altitude ranges of the Mau Forest Complex: 2000 m (annual rainfall of 1000 mm), 2300 m (1500 mm), 2500 m (western Mau flank, annual rainfall greater than 2000 mm) above sea level. The Western flanks of the Mau Forest contain plants that are particularly preferred for preparing the herbal compositions of the invention. The plants grown in the drier. Eastern flank of the Mau Forest Complex also may be used.

Plant material for preparing compositions of the invention may also be obtained from plants grown in a greenhouse environment. The germination of the seeds of particular plants may be altitude or soil dependent. Seeds for greenhouse planting may require collection from the natural dispersal agents as they exist in the wild. Additionally, simulation of rainfall, sunlight (an average of 12 hours per day in the Mau Forest Complex), and soil conditions of the Mau Forest Complex (i.e., rich volcanic loam having a pH between 3.8-5.8) may be required to obtain plants of similar potency.

The seeds of *abyssinica* (representative seed of said line having been deposited under ATCC Accession No. PTA-6969) are contained in a fleshy fruit. There are about 4 seeds enclosed by the flesh. A ripe fleshy fruit can be soaked in water for about 4 days, to make it possible to squeeze with minimum force to release the small seeds, each being approximately the size of a tomato seed or slightly larger. The seeds are then washed, dried and stored, awaiting germination under Mau Forest-like environmental conditions. In the wild, the fruit flesh is soaked by rain water, which results in the release of the seeds. The seeds grow naturally under the environmental conditions of the Mau Forest Complex as described above.

The *Clutia robusta* (representative seed of said line having been deposited under ATCC Accession No. PTA-6970) seeds are much smaller and encased in berries having a nut-like outer covering which encases approximately 3 to 4 seeds the size of a grain of sand. When mature seeds are exposed direct sunlight, they disperse rapidly in a process called explosive dispersal. This is not a problem in the wild, but if one is interested in collecting the seeds, care and intelligence are required, or else all the seeds will fly away under the scattering effect of the hot sun.

To recover the *clutia robusta* seeds, the berries should be placed in a metallic container, and covered with a material that allows sunlight to enter, such as a transparent polyethylene film surrounding a container of appropriate wire mesh. Exposure to light will cause the shells to break open, releasing the seeds which can then be separated from the chaff.

The optimal time for planting the *clutia* and *dovyallis* seeds in their natural environment is during the long rains, typically around the month of April. However, in the wild, the plants will generally grow throughout the year, except during the dry season, as the plants require a considerable amount of water and light to grow.

*Croton macrostachyus* produces pale pea-sized capsules, on drooping spikes to 30 cm long, splitting open on the tree to release 3 shiny grey seeds, covered at one end by a soft, creamy aril, or envelope.

*Prunus africana* produces spherical fruit, about 10 mm in diameter and is pinkish brown in color.

The *Acacia nilotica* (representative seed of said line having been deposited under ATCC Accession No. PTA-7378) plant produces straight or curved pods measuring approximately 17×2 cm. When young, the pods are green and fleshy but get darker with age, and are usually velvety. Pods have a fruity odor and open on the ground to release seeds.

*Ekebergia capensis* produces rounded, thin skinned berries, up to 2.5 cm in diameter, on long stalks in heavy bunches, which are yellow to red in color when mature.

The berry-like fruits of *Rhamnus prinoides* are approximately the size of a pea (about 5 mm in diameter), roundish and clearly divided into three compartments. They are fleshy and green, turning red and then purple as they ripen.

The fruit of the *Asparagus africanus* is a round berry, approximately 0.5 cm in diameter, green aging to orange, found most of the year. It is spread mainly by birds carrying the seeds.

The *Anthocleista grandiflora* produces fruits that are oval in shape, measuring approximately 3 cm×2 cm, glossy, smooth and brown when mature. Multi-seeded, large fruits are found throughout the year.

The *Bersama abyssinica* produces a smooth, spherical capsule, measuring approximately 2.5 cm in diameter, golden velvety at first, losing most of the hair and becoming brown by maturity; splitting into four valves to reveal attractive bright red seeds, about 10 mm long, enveloped for about their half length by a yellow, cup-shaped aril.

*Adenia gummifera* produces a fruit which is a stalked 3-valved capsule, leathery or fleshy, often red; seeds compressed with bony testa in a fleshy aril.

*Plantago palmata* (representative seed of said line having been deposited under ATCC Accession No. PTA-7377) produces a capsule-like fruit with two seeds per capsule.

*Periploca linearifolia* (representative seed of said line having been deposited under ATCC Accession No. PTA-7375) produces black seeds measuring approximately 10 mm long and 2 mm wide with white wool measuring around 3 cm attached to the tips of the seeds. The seeds are enclosed in pods measuring about 12 cm long. Upon maturity, the pods break open upon exposure to sunlight. This releases the seeds, which are borne aloft by the wool as they are dispersed by wind. Alternatively, these plants may be cultivated from stem cuttings, which when laid on or planted in the ground, grow roots and propagate new plants.

*Clematis hirsuta* (representative seed of said line having been deposited under ATCC Accession No. PTA-7383) produces yellowish seeds measuring approximately 3mm in length and 1 mm in breadth. The seeds are surrounded by yellowish-white wool which measures about 5 mm long. The wool carries the seeds upon the wind, which is the dispersal agent.

HIV Testing

As noted previously, for purposes of this application, a person is considered HIV-negative if the subject tested negative on a two-part HIV screening tests, consisting of an initial screening test and a confirmatory test.

An infected individual usually goes for testing for one or more of the following reasons: 1) the individual feels ill, 2) the individual's sexual partner is ill and has tested positive, 3) the individual's sexual partner died of AIDS; or 4) the individual suspects his/her sexual partner is sexually promiscuous.

The initial screening test is ELISA (Enzyme-Linked Immunosorbent Assay), an enzyme immunoassay (EIA) to determine the presence of HIV antibodies. The ELISA test uses artificial HIV proteins that capture antibodies to the virus and is more than 99 percent accurate. If antibodies to HIV are present (positive result), the test is typically repeated. However, other antibodies can cause a false-positive result.

Generally, HIV-1 antibodies are detectable approximately 25 days after acute infection, with nearly all infected subjects testing HIV positive 12 weeks after infection. The process of developing antibodies to a virus is termed seroconversion, and individuals who become antibody-positive are often called seroconverters.

Two types of HIV have been identified: HIV-1 and HIV-2, of which, HIV-1 is more common. HIV-1 and HIV-2 are similar in the modes of transmission (sexual contact, sharing needles, etc.) and infected individuals are generally subject to the same opportunistic infections. However, HIV-2 appears to weaken the immune system more slowly than HIV-1.

In Kenya, individuals are generally tested for antibodies to both HIV-1 and HIV-2. HIV-1 is generally more common in the Western world and HIV-2 is more common in Africa. In Kenya however, most HIV-positive individuals have the HIV-1 infection. It is believed that 90% of the HIV-positive cases in Kenya are HIV-1, with the remaining 10% of HIV-positive cases being the HIV-2. While rare, subjects occasionally are HIV antibody-positive to both types of HIV (i.e. HIV-1 and HIV-2).

The second part of the HIV screening test is called the confirmatory test. In the U.S., the most often used confirmatory test is the Western blot, wherein an electrical field is used to separate the various components by their molecular weight prior to evaluating antibody binding. This allows identification of antibodies to specific viral antigens, which show up as identifiable "bands" on a strip of test paper. The Western blot test is more difficult to perform and accurately interpret than the ELISA test, but it is less likely to give a false-positive result because it can distinguish HIV antibodies from other antibodies that may react to the ELISA. Other confirmatory tests may be used, including the indirect fluorescent antibody assay (IFA) and the radioimmunoprecipitation assay (RIPA).

One major drawback of antibody tests is the "window" period (i.e. the time it takes the body to produce antibodies after infection has begun). The screening tests do not correlate to the presence or absence of symptoms. The standard HIV tests do not detect the virus itself, but instead detect the antibodies that the body produces in response to the virus. During the period before the antibodies are produced, a person may be infected with HIV and can infect others, and still test negative on the HIV antibody test. It is therefore important to tell subjects who test negative to avoid engaging in high-risk behavior and to return for retesting at a later date.

The p24 antigen test can be used in diagnosing HIV early in the course of infection. It is primarily used to screen the blood supply but in some places it is used for testing for HIV. The p24 antigen is a protein that is part of the HIV. Early in the infection, it is produced in excess and can be detected in the blood serum by a commercial test. The p24 test can detect HIV infection before the HIV antibody test can and it is recommended 2-3 weeks after a risk exposure.

Individuals that test positive for HIV are regularly administered two tests to monitor HIV levels in the blood and to determine how the virus is affecting the immune system. These tests are: (1) a viral load measurement, and (2) CD4+ cell counts.

Viral load measurement (also called the HIV plasma RNA test) determines how many HIV viral particles are present in a given amount of a person's blood. Test results help determine the best treatment for the HIV infection as the viral load test shows how fast the virus is multiplying in the body. Because HIV reproduces by making copies of itself, the results are given as copies per milliliter (mL). Viral load testing can also reveal the presence HIV infection before antibodies can be detected and can also accurately determine whether a baby born to an infected mother has HIV.

CD4+ cell counts (T-lymphocyte measurements) provide an estimate of the immunologic status of an individual and help determine the immediate risk of opportunistic infection. The CD4+ count measures the number of a certain type of white blood cell that is most affected by HIV, and are measured every 3 to 4 months in individuals infected with HIV. On average, an individual infected with HIV loses approximately, 30-60 CD4+ cells per year, although in some subjects, CD4+ T-lymphocyte counts may remain stable for years followed by rapid decline.

CD4(T4) or CD4+ cells are a type of T cell involved in protecting against infections, such as for example, viral, fungal, and protozoal infections. Destruction of these cells is the major cause of immunodeficiency observed in AIDS, and decreasing CD4+ lymphocyte counts appear to be the best indicator for the potential development of opportunistic infections. In judging the severity of HIV/AIDS cases, the CD4+ lymphocyte count is more indicative of the severity of the disease than gross symptomalogy, although it is also true that certain symptoms may be associated with particular CD4+ lymphocyte levels. See, for example, FIG. 1. Average normal adult CD4+ cell counts typically ranges from 500 to 1,500/2,000 cells per cubic milliliter of blood.

As CD4+ cell counts decrease below the normal adult levels during primary HIV infection, CD8+ or cytotoxic T-lymphocytes also increase. However, most studies indicate that an increase in CD8 count is not a prognostic indicator of disease progression. Some clinicians in the U.S. use the CD4/CD8 ratio as an indicator of disease progression, however, this ratio varies not only with the severity of the disease, but with the ethnicity of the subject.

There are several systems for classifying and staging HIV infection. The most commonly-used system is the CDC (Centers for Disease Control) Scheme. The CDC scheme has three classifications based upon CD4 counts. The definitions of the three CD4+ T-lymphocyte categories I as follow: Category 1: >500 cells/mm$^3$ (or CD4%>28%); Category 2: 200-499 cells/mm$^3$ (or CD4% 14%-28%); and Category 3: <200 cells/mm$^3$ (or CD4%<14%).

In addition to the CDC classification scheme, there are also 3 possible categories of clinical conditions, which are designated by the letters A, B and C. Therefore, a given individual can have the following CDC classification and clinical categorization designation: 1-A, or 1-B, or I-C, 2-A, 2-B, 2-C, 3-A, 3-B or 3-C.

An individual in category A is identified as an adolescent or adult (>13 years) with documented HIV infection having one or more of the following conditions (and lacking any of the conditions associated with categories B and C): asymptomatic HIV infection; persistent generalized lymphadenopathy; and acute (primary) HIV infection with accompanying illness or history of acute HIV infection.

An individual in category B is identified as an adolescent or adult (>13 years) with documented HIV infection having one or more of the following conditions (and lacking any of the conditions associated with category C) and that meet at least one of the following criteria: (a) the conditions are attributed to HIV infection or are indicative of a defect in cell-mediated immunity; or (b) the conditions are considered by physicians to have a clinical course or to require management that is complicated by HIV infection. Examples of conditions in clinical category B include but are not limited to: bacillary angiomatosis; candidiasis (oropharyngeal, i.e. thrush); candidiasis (vulvovaginal, persistent, frequent, or poorly responsive to therapy); cervical dysplasia (moderate or severe/cervical carcinoma in situ); constitutional symptoms, such as fever (body temperature of 38.5° C. or greater) or diarrhea lasting longer than 1 month; hairy leukoplakia (oral); herpes zoster (shingles), involving at least two distinct episodes or more than one dermatome; idiopathic thrombocytopenic purpura; listeriosis; pelvic inflammatory disease (particularly if complicated by tubo-ovarian abscess); and (11) peripheral neuropathy. For classification purposes, Category B conditions take precedence over Category A conditions. For example, an individual previously treated for oral or persistent vaginal candidiasis (but not exhibiting a Category C disease or condition) who is now asymptomatic, should be classified in Category B.

An individual in category C is identified as an adolescent or adult (>13 years) with documented HIV infection having one or more of the following conditions Category C conditions include the following: candidiasis of bronchi, trachea, or lungs; candidiasis (esophageal); invasive cervical cancer; coccidioidomycosis (disseminated or extrapulmonary); cryptococcosis (extrapulmonary); cryptosporidiosis (chronic intestinal, greater than 1 month's duration); cytomegalovirus disease (other than liver, spleen, or nodes); cytomegalovirus retinitis (with loss of vision); encephalopathy (HIV-related); herpes simplex: chronic ulcer(s) (greater than 1 month's duration), or bronchitis, pneumonitis, or esophagitis; histoplasmosis (disseminated or extrapulmonary); isosporiasis (chronic intestinal, greater than 1 month's duration); Kaposi's sarcoma; lymphoma (Burkitt's, or equivalent term), lymphoma, (immunoblastic, or equivalent term); Lymphoma (primary, of brain); mycobacterium avium complex or M. kansasii, disseminated or extrapulmonary; mycobacterium tuberculosis, (any site, pulmonary or extrapulmonary); mycobacterium, (other species or unidentified species, disseminated or extrapulmonary); pneumocystis carinii pneumonia; pneumonia (recurrent); progressive multifocal leukoencephalopathy; *Salmonella* septicemia (recurrent); toxoplasmosis of brain; and wasting syndrome due to HIV. For classification purposes, once a Category C condition has occurred, the individual will remain in Category C.

One method of treatment for HIV-positive individuals is the highly active antiretroviral therapy (HAART) regimen. HAART is a therapeutic treatment regime consisting of the combination of anti-HIV drugs, that is prescribed to HIV-positive individuals even before they develop symptoms of AIDS. The therapy usually includes one nucleoside analog, one protease inhibitor and either a second nucleoside analog or a non-nucleoside reverse transcription inhibitor (NNRTI). Frequently, the HAART regime is toxic to the individual, resulting in adverse side effects. For example, HAART can be toxic to blood because it almost always includes one or two nucleoside analogs, like AZT that are notorious for their toxicity to red and white blood cells and blood cell production. Various forms of anemia are very common and sometimes are irreversible. However, it is extremely rare for a subject on the HAART regimen reverse his/her HIV status in Kenya.

Examples of drugs administered for the HAART treatment regime include: azidovudine (AZT), didanosine (dideoxyinosine, ddI), zalcitabine (dideoxycytosine, ddC), lamivudine (epivir, 3TC), nevirapine (Viramune), abacavir (Ziagen), stavudine (Zerit, d4T), tenofovir (Viread), efavirenz (Sustiva), amprenavir (Agenerase), lopinavir (Kaletra), nefinavir (Viracept), saquinavir (Invirase), ritonavir (Norvir), indinavir (Crixivan), and delavirdine (Rescriptor).

Method for Extracting Alkaloid Compounds and Preparing Herbal Composition

The compositions of the invention are prepared using roots of *abyssinica* and *Clutia robusta*, and optionally one or more of the following: the stem bark of *Prunus africana*, stem bark of *Croton macrostachyus*, stem bark of *Acacia nilotica*, roots of *Rhamnus prinoides*, roots of *Adenia gummifera*, roots of *Asparagus africanus*, stem bark of *Anthocleista grandiflora*, whole plant of *Plantago palmata*, roots of *Clematis hirsuta*, stem bark of *Ekebergia capensis*, stem bark of *Bersama abyssinica*, and roots of *Periploca linearifolia*. Preferably, the ingredients collected are fresh, although dried samples may also be used. The ingredients are combined and chopped into small pieces and dried. Preferably, the dried ingredients are ground into a fine powder after drying. Alternatively, each ingredient may be processed individually and combined at a later stage. Preferably, if combined for the extraction process, the ingredients are combined in equal weight ratios. Optionally, *Dovyalis abyssinica, Clutia robusta, Prunus africana, Croton macrostachyus, Acacia nilotica, Rhamnus prinoides, Adenia gummifera, Asparagus africanus, Anthocleista grandiflora, Plantago palmata, Clematis hirsuta, Ekebergia capensis, Bersama abyssinica* and *Periploca linearifolia* can be present in a weight ratio of 2:2:2:2:2:2:1:2:2:1:2:2:2:2.

The herbal plant material mixture may be extracted with a non-polar solvent to remove fats from the chopped herbal ingredients. Preferably, approximately 20% by volume non-polar solvent is added to the herbal ingredient mixture. Non-polar solvents are generally organic solvents having a dielectric constant less than 20. Non-polar solvents that may be used include, but are not limited to: alkanes, 1,4-dioxane, carbon tetrachloride, chloroform, methylene chloride, benzene, ethers, ethyl acetate, tetrahydrofuran, acetic acid, butanol, chlorobenzene, cycloalkanes, xylene, and the like. Preferred non-polar solvents are xylene and ether.

The non-polar solvent is decanted and discarded. The defatted herbal solids, are then allowed to dry. Sufficient base is added to the defatted herbal material to achieve a pH of approximately 8. The concentration of the base added can be adjusted to provide sufficient liquid volume to cover the defatted herbal solid mixture. Any suitable base may be used, with preferred bases including NaOH, KOH, $Ca(OH)_2$, $Mg(OH)_2$, $NH_4OH$, and the like. The base extract is then heated for 2-4 hours. Preferably, the ingredients are slowly simmered under reflux conditions, although the same effect can be achieved by simmering the mixture in a covered pot.

Acid is added to the base extract to achieve a pH of approximately 3. Preferably the acid is HCl, although other acids, including but not limited to, HBr, $HNO_3$, $H_2SO_4$, $H_3PO_4$, or any other acid suitable for achieving a pH of approximately 3 may be used as well. The concentration of the acid can be adjusted as necessary to provide sufficient volume to the mixture. The acidified solution is then boiled for approximately 2-4 hours under the same conditions employed for the heating of the basic solution. After heating, the mixture is cooled, and the aqueous layer is separated from the mixture, such as for example, by decanting the liquid from the remaining solids. Acid is then added to the remaining residue sufficient to achieve a pH of approximately 3, and the mixture is then reheated for approximately 2-4 hours under the same conditions previously employed. The aqueous layer is separated from the ingredients and the two acidified layers are combined. If necessary, additional acid extractions may be performed.

The acidic filtrate is extracted several times with a non-polar solvent until little or no emulsion forms. Preferable non-polar solvents are ether and xylene. Base is added to the aqueous layer to precipitate the alkaloid compounds. Preferably, base is added to achieve a pH of approximately 9. The precipitate is separated from the aqueous solution, neutralized and dried.

The precipitate is preferably collected in either crystalline or powder form, and may administered to an subject as a beverage, capsule, tablet, powder, candy, gel, nutritional product or pharmaceutical product.

The precipitate can be further purified as desired to isolate individual alkaloid compounds by any known chromatographic means.

It is understood that at any point during the process of extracting the alkaloid compounds from the herbal ingredients that the aqueous solution can be concentrated and stored for later use without the need for precipitation of the compounds from solution.

Alternatively, the alkaloid compounds for use in the present invention can be synthesized by known methods once the chemical structure has been determined. Isolated compounds can be analyzed by chemical analysis, mass spectroscopy, infrared spectroscopy, X-ray diffraction, NMR (including $^1$H NMR, $^{13}$C NMR, COSY, NOSEY, and the like), and other known analytical techniques to obtain the chemical structures. For example, chemical structures for four extracts obtained from *abyssinica* have been previously determined. (See, for example, http://www.dfuni.dk/uploads/media/Naturstofgruppen_BonnieRasmussen.pdf).

The invention will now be described in greater detail by reference to the following non-limiting examples.

EXAMPLES

Determination of Bioactivity of Plant Extracts

The efficacy of the individual plant extracts were tested against *Escherichia coli* and *Staphylococcus aureus*. Plant extracts were obtained as described above. Solutions containing 100 ppm (parts per million) of each plant extract were prepared for use in the anti-bacterial assay.

Preparation of bacterial culture of *Escherichia coli* and *Staphylococcus aureus*.

Standard cultures of *E. coli* (representing gram-negative strains of bacteria) and *Staphylococcus aureus* (representing gram-positive bacteria) were obtained from Moi University Teaching and Referral Hospital. Assays were conducted at the Moi University Department of Botany.

Bioassay procedure (Diffusion Method)

Nutrient agar was used as growth medium for both bacteria samples. The agar was sterilized in an autoclave at 120° C., cooled and poured into sterile Petri dishes and allowed to set. Sterile conditions were achieved and maintained by exposing the area to a UV lamp during sample preparation and the assay the procedure.

The cooled agar medium was streaked on the surface with each bacteria culture. Wells were dug in the middle of the medium, using a cork borer, where the prepared plant extract was deposited. A control experiment was also performed, using plain sterile water in place of the plant extracts.

Cultures were incubated for 12 hours, after which zones of inhibition of bacterial growth were determined and measured. Bacteria-growth inhibition was expressed in diameters (mm), and was determined by measuring the distance from edge of the well to area where the bacteria begin to show growth. Generally, the larger inhibition diameter indicates greater potency of the particular extract against the bacteria.

Of the 23 plants were screened in this assay, 14 of the plants had bacteria growth inhibition diameters greater than 8 mm, which was previously determined to be the minimum activity required for adoption of the extract for the herbal remedy. The anti-bacterial activities of the plants were compared with standard antibiotics. Of the 14 plants having inhibition diameters greater than 8 mm, *abyssinica* and *Clutia robusta* demonstrated the greatest anti-bacterial activity. Results for plant extracts exhibiting inhibition diameters greater than 8 mm are provided in the Table 1.

TABLE 1

Zones of Inhibition Expressed as Inhibition Diameter (mm)

|  | Plant Name | E. coli | S. aureus |
|---|---|---|---|
| 1. | Dovyalis abyssinica | 17.2 | 16.6 |
| 2. | Clutia robusta | 16.7 | 15.8 |
| 3. | Prunus Africana | 14.7 | 14.6 |
| 4. | Croton macrostachyus | 14.7 | 14.4 |
| 5. | Acacia nilotica | 13.6 | 13.2 |
| 6. | Ekebergia capensis | 12.8 | 13.0 |
| 7. | Clematis hirsuta | 11.9 | 12.8 |
| 8. | Adenia gummifera | 11.7 | 12.8 |
| 9. | Asparagus africanus | 11.3 | 11.2 |
| 10. | Plantago palmata | 11.0 | 11.0 |
| 11. | Rhamnus prinoides | 10.9 | 10.8 |
| 12. | Periploca linearifolia | 10.9 | 10.6 |
| 13. | Bersama abyssinica | 10.5 | 10.3 |
| 14. | Anthocleista grandiflora | 10.0 | 9.7 |

Administration of the Herbal Composition

The plant extract precipitates are preferably purified and collected in either crystalline or powder form. The precipitates can administered to a subject as a beverage, capsule, tablet, powder, candy, gel, nutritional product or pharmaceutical product. Preferably, between 0.1 and 25 grams of alkaloids are administered per day to an infected subject. The herbal composition is preferably administered as a beverage wherein approximately 1 tbsp of powdered extract is dissolved in approximately 250 mL of hot water, and drunk. Dosing is either twice daily at 12 hour intervals, or three times daily at eight hour intervals (depending on the level of infection of the test subject), and is preferably administered with a meal.

Subjects in the current trials were screened at the Walter Reed Hospital of the U.S. Army in Kericho, Kenya, the Moi University Hospital in Eldoret, and at various Voluntary Counseling and Testing (VCT) Centers scattered throughout the country.

Subjects' CD4 and CD8 counts were measured using a FACSCount™ system following procedures provided in the FACSCount White Paper (July 1994). HIV-1 and HIV-2 antibodies were detected using a bioMérieux Vironostika® HIV Uni-Form II Ag/Ab ELISA system.

All subjects administered the herbal composition were HIV-positive adults. Prior to administration of the herbal composition, an initial CD4 count for each subject was determined, followed by an assessment of the level of opportunistic infections. Those with fewer opportunistic infections were administered the herbal composition twice daily after meals, at twelve hour intervals. Those with more opportunistic infections were administered the herbal composition three times daily, at 8 hours intervals. Each subject was given one week's dosage during each visit to the clinic. This was done to make it possible to monitor compliance, and to avoid the possibility of subjects sharing the drug with others.

Example 1

Initial studies for the treatment of HIV positive subjects with herbal remedy were conducted by treating four HIV positive subjects with two different herbal remedies. Two subjects were administered a herbal composition which included the extract of *abyssinica*, while the other two subjects were administered a herbal remedy which included the extract of *Clutia robusta*. The subjects were each treated for a period of three months. The CD4 counts of both sets of subjects (i.e., those administered either *abyssinica* or *Clutia robusta*) increased by approximately 10 per month of treatment.

Example 2

In another study, three subjects were administered a herbal composition prepared with a 1:1 ratio by weight mixture of *Doyalis abyssinica* and *Clutia robusta* for a period of approximately three months. The CD4 counts of the subjects treated with the mixture increased by approximately 30 per month.

Example 3

In yet another experiment, 20 subjects were administered a herbal composition containing extracts of *abyssinica, Clutia robusta, Prunus africana, Croton macrostachyus, Acacia nilotica, Ekebergia capensis, Clematis hirsuta* and *Adenia gummifera*. The 8 plant extracts were selected from 23 total plant extracts which had been previously assayed against *E. coli* and *S. aureus*. As shown in Table 2, CD4 counts increased of subjects by up to 100 per month, but none of the subjects tested HIV negative within the three-month period.

TABLE 2

| Subject ID | $CD_{A/ul}$ per month | | | | |
|---|---|---|---|---|---|
|  | Month 1 | Month 2 | Month 3 | Month 4 | Month 5 |
| 1b | 118 | 150 | 399 | 420 | — |
| 2b | 100 | 250 | 420 | 460 | — |
| 3b | 04 | 93 | 190 | 320 | — |
| 4b | 667 | 550 | 815 | 830 | — |
| 5b | 160 | 120 | 480 | 620 | — |
| 6b | 210 | 190 | 520 | 510 | — |
| 7b | 420 | 500 | 780 | 780 | — |
| 8b | 128 | 108 | 310 | 304 | — |
| 9b | 110 | 150 | 380 | 348 | — |
| 10b | 380 | 460 | 716 | 716 | — |
| 11b | 300 | 410 | 390 | 560 | — |
| 12b | 100 | 120 | 310 | 318 | — |
| 13b | 250 | 180 | 340 | 420 | — |
| 14b | 80 | 70 | 260 | 380 | — |
| 15b | 140 | 110 | 300 | 420 | — |
| 16b | 250 | 180 | 290 | 360 | — |
| 17b | 300 | 380 | 460 | 580 | — |
| 18b | 280 | 290 | 290 | 410 | — |
| 19b | 118 | 190 | 170 | 320 | — |
| 20b | 160 | 160 | 220 | 299 | 360 |

Example 4

In another experiment, 26 HIV-positive subjects were treated with a herbal composition consisting of the 14 herbal ingredients identified in Table 1. Subjects were administered a composition prepared by dissolving approximately 1 tbsp. (or 15 ml) of the powdered ingredients (a mixture prepared the 14 plants listed in Table 1) in approximately 8 ozs. (250 ml) of hot water. The supernatant liquid was then ingested by the subject.

The subjects were divided into two groups: the first group having 10 subjects (subject ID Nos. 1-10) and the second group having 16 subjects (Subject ID Nos 11-26). In the first group, each the 14 plants was present in the composition in equal weight ratios. In the second group, the concentrations of abyssinica and Clutia robusta were approximately half of the other 12 ingredients as disclosed.

As shown in Table 3, CD4 counts for each subject were measured on a monthly basis. The CD4 counts of the test subjects treated with the 14 ingredient herbal composition increased by up to 100 per month. Six subjects tested HIV-negative after four months of treatment. Two subjects tested HIV-negative after two months of treatment.

TABLE 3

| Subject | $CD_{4/\mu L}$ per month | | | |
|---|---|---|---|---|
| ID | Month 1 | Month 2 | Month 3 | Month 4 |
| 1 | 420 | 450 | 570 | HIV negative |
| 2 | 320 | 390 | 480 | 520 |
| 3 | 100 | 115 | 250 | — |
| 4 | 80 | 150 | 310 | — |
| 5 | 340 | 370 | 480 | 560 |
| 6 | 120 | 180 | 299 | — |
| 7 | 118 | 350 | 360 | HIV negative |
| 8 | 125 | 105 | 225 | — |
| 9 | 300 | 200 | 400 | HIV negative |
| 10 | 280 | 399 | 410 | HIV negative |
| 11 | 400 | 500 | 520 | HIV negative |
| 12 | 250 | 250 | 310 | — |
| 13 | 250 | 460 | 600 | — |
| 14 | 400 | 520 | 780 | — |
| 15 | 250 | 330 | 480 | HIV negative |
| 16 | 667 | 550 | 815 | 830 |
| 17 | 150 | 250 | 380 | — |
| 18 | 620 | 640 | 660 | — |
| 19 | 310 | 400 | 480 | — |
| 20 | 243 | 245 | 280 | — |
| 21 | 180 | 216 | 434 | — |
| 22 | 280 | 390 | — | — |
| 23 | 360 | 420 | — | — |
| 24 | 190 | 280 | — | — |
| 25 | 630 | 720; HIV negative | — | — |
| 26 | N/A; HIV positive | N/A; HIV negative | — | — |

By comparison with the results achieved with the present invention, in a study conducted on subjects on HAART in Moi University Teaching and Academic Model for Prevention and Treatment of HIV (AMPATH), the CD4 count increases were gradual, generally taking several years to reach above 500. The subjects were treated with conventional antiretroviral (ARV) therapy, consisting of twice daily dosing of Stavudine, Lamivudine and Nevirapine (d4T-3TC-NVP). Other ARV regimes include treatment with combinations consisting of ZDV-3TC-NVP, d4T-3TC-EFV and ZDV-3TC-EFV (wherein ZDV is Zidovudine and EFV is Efavirenz). Treatment guidelines are provided in the publication "Integrated Management of Adolescent and Adult Illness," published in January 2004 by the World Health Organization. ARV therapy subjects rarely reverse their seroconversion status, and among those listed in Table 4, none did so.

TABLE 4

Comparative Results of CD4 Count Increases in Subjects Under Conventional ARV Therapy.

| | 6 Months | 1 Year | 1½ Years | 2 Years | 2½ Years | 3 Years |
|---|---|---|---|---|---|---|
| 1. | 247 | 207 | 264 | 197 | 138 | 367 |
| 2. | 315 | 327 | 150 | 260 | — | — |
| 3. | 268 | 199 | 195 | 360 | — | — |
| 4. | 99 | 163 | — | — | — | — |
| 5. | 265 | 40 | 36 | 247 | 332 | 397 |
| 6. | 138 | 311 | 584 | 578 | — | — |
| 7. | 37 | 298 | — | — | — | — |
| 8. | 201 | 261 | — | — | — | — |
| 9. | 21 | 52 | 74 | 309 | — | — |
| 10. | 2 | 156 | — | — | — | — |
| 11. | 43 | 200 | — | — | — | — |
| 12. | 169 | 295 | — | — | — | — |
| 13. | 75 | 144 | 179 | — | — | — |

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Definitions provided herein are not intended to be limiting from the meaning commonly understood by one of skill in the art unless indicated otherwise.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The plant parts described in the specification are those in which in the experience of the inventors, the highest concentration of beneficial ingredients are to be found. However, it will be apparent to those skilled in the art that the same or other beneficial compounds may be found in other parts of the recited plants not specifically recited in paragraph [0022] above and elsewhere in this application, and that therefore, any composition comprised of any part or parts of the recited plants which includes *abyssinica* and *Clutia robusta* is within the scope of the invention.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A composition comprising:
   dried root of *abyssinica*;
   and dried root of *Clutia robusta*.

2. The composition of claim 1, further comprising at least 1 herb selected from the group consisting of: dried stem bark of *Prunus africana*, dried stem bark of *Croton macrostachyus*, dried stem bark of *Acacia nilotica*, dried root of *Rhamnus prinoides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, and dried root of *Periploca linearifolia*.

3. The composition of claim 1 further comprising dried stem bark of *Prunus africana*, dried stem bark of *Croton macrostachyus*, dried stem bark of *Acacia nilotica*, dried root of *Rhamnus prinoides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, and dried root of *Periploca linearifolia*.

4. A water extract of the composition of any one of claims 1-3.

5. The composition of claim 1, wherein the dried root of *abyssinica* and the dried root of *Clutia robusta* are in a weight ratio of 1:1.

6. The composition of claim 3, wherein said dried root of *Dovyalis abyssinica*, said dried root of *Clutia robusta*, said dried stem bark of *Prunus africana*, said dried stem bark of *Croton macrostachyus*, said dried stem bark of *Acacia nilotica*, said dried root of *Rhamnus prinoides*, said dried root of *Adenia gummifera*, said dried root of *Asparagus africanus*, said dried stem bark of *Anthocleista grandiflora*, said dried whole plant of *Plantago palmata*, said dried root of *Clematis hirsuta*, said dried stem bark of *Ekebergia capensis*, said dried stem bark of *Bersama abyssinica* and said dried root of *Periploca linearfolia* are in a weight ratio of 2:2:2:2:2:2:1:2:2:1:2:2:2.

7. A water extract of the composition of claims 5 or 6.

8. An herbal pharmaceutical composition comprising a non-polar extract of *abyssinica* root and *Clutia robusta* root.

9. The herbal pharmaceutical composition of claim 8, further comprising a non-polar extract of at least one herb selected from the group consisting of: dried stem bark of *Prunus africana*, dried stem bark of *Croton macrostachyus*, dried stem bark of *Acacia nilotica*, dried root of *Rhamnus prinoides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, and dried root of *Periploca linearifolia*.

10. The herbal pharmaceutical composition of claim 37, further comprising a *non-polar* extract of dried stem bark of *Prunus africana*, dried stem bark of *Croton macrostachyus*, dried stem bark of *Acacia nilotica*, dried root of *Rhamnus prinoides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, and dried root of *Periploca linearifolia*.

11. The herbal pharmaceutical composition of claim 8, further comprising a non-polar extract of at least 1 herb selected from the group consisting of: stem bark of *Prunus Africana*, stem bark of *Croton macrostachyus*, stem bark of *Acacia nilotica*, root of *Rhamnus prinoides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

12. The herbal pharmaceutical composition of claim 8, further comprising a non-polar extract of stem bark of *Prunus Africana*, stem bark of *Croton macrostachyus*, stem bark of *Acacia nilotica*, root of *Rhamnus prinoides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

13. The composition of claim 8, wherein the root of *Dovyalis abyssinica* and the root of *Clutia robusta* are in a weight ratio of 1:1.

14. The composition of claim 12, wherein said root of *Dovyalis abyssinica*, said root of *Clutia robusta*, said stem bark of *Prunus africana*, said stem bark of *Croton macrostachyus*, said stem bark of *Acacia nilotica*, said root of *Rhamnus prinoides*, said root of *Adenia gummifera*, said root of *Asparagus africanus*, said stem bark of *Anthocleista grandiflora*, said whole plant of *Plantago palmata*, said root of *Clematis hirsuta*, said stem bark of *Ekebergia capensis*, said stem bark of *Bersama abyssinica* and said root of *Periploca linearfolia* are in a weight ratio of 2:2:2:2:2:2:1:2:2:1:2:2:2:2.

* * * * *

UNITED STATES PATENT AND TRADEMARK OFFICE
CERTIFICATE OF CORRECTION

| | | |
|---|---|---|
| PATENT NO. | : 7,556,830 B2 | Page 1 of 1 |
| APPLICATION NO. | : 11/352931 | |
| DATED | : July 7, 2009 | |
| INVENTOR(S) | : Paul Kiprono Chepkwony, Maria Medina and Mitchell Medina | |

It is certified that error appears in the above-identified patent and that said Letters Patent is hereby corrected as shown below:

In the Abstract, Line 4 the word Dovyalis should appear before abyssinica.

The word Dovyalis should appear before abyssinica in the following places:
Column 4, line 11
Column 4, line 26-27
Column 5, line 9
Column 5, line 22
Column 7, line 26
Column 8, line 39
Column 13, line 16
Column 14, line 38
Column 15, line 18
Column 16, line 15
Column 16, line 19
Column 16, line 33
Column 19, line 14
Column 19, line 38
Column 19, line 54

Column 4, line 30 -- there should be a space between "africana" and "stem".
Column 8, line 62, the word "Clutia" should be capitalized.
Column 9, line 1, the words "Clutia" and "Dovyalis" both should be capitalized.
Column 9, line 31, the dimensions given should read 3 cm x 2 cm.

Claim 10, should depend from claim 8, not the non-existent claim 37.
Claim 10, line 13, the word "non-polar" should be in plain type, not italics.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,556,830 B2 |
| APPLICATION NO. | : 11/352931 |
| DATED | : July 7, 2009 |
| INVENTOR(S) | : Paul Kiprono Chepkwony, Maria Medina and Mitchell Medina |

It is certified that error appears in the above-identified patent and that said Letters Patent is hereby corrected as shown below:

In the Abstract, Line 4 the word Dovyalis should appear before abyssinica.

The word Dovyalis should appear before abyssinica in the following places:
Column 4, line 11
Column 4, line 26-27
Column 5, line 9
Column 5, line 22
Column 7, line 26
Column 8, line 39
Column 13, line 16
Column 14, line 38
Column 15, line 18
Column 16, line 15
Column 16, line 19
Column 16, line 33
Column 19, line 14
Column 19, line 38
Column 19, line 54

Column 4, line 30 -- there should be a space between "africana" and "stem".
Column 8, line 62, the word "Clutia" should be capitalized.
Column 9, line 1, the words "Clutia" and "Dovyalis" both should be capitalized.
Column 9, line 31, the dimensions given should read 3 cm x 2 cm.

UNITED STATES PATENT AND TRADEMARK OFFICE
CERTIFICATE OF CORRECTION

PATENT NO. : 7,556,830 B2
APPLICATION NO. : 11/352931
DATED : July 7, 2009
INVENTOR(S) : Paul Kiprono Chepkwony, Maria Medina and Mitchell Medina It is certified that error appears in the above-identified patent and that said Letters Patent is hereby corrected as shown below:

Column 20, Claim 10, line 12, should depend from claim 8, not the non-existent claim 37.
Column 20, Claim 10, line 13, the word "non-polar" should be in plain type, not italics.

This certificate supersedes the Certificate of Correction issued September 15, 2009.

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

PATENT NO.       : 7,556,830 B2
APPLICATION NO.  : 11/352931
DATED            : July 7, 2009
INVENTOR(S)      : Paul Kiprono Chepkwony, Maria Medina and Mitchell Medina It is certified that error appears in the above-identified patent and that said Letters Patent is hereby corrected as shown below:

In the Abstract, Line 4 the word Dovyalis should appear before abyssinica.

The word Dovyalis should appear before abyssinica in the following places:
Column 4, line 11
Column 4, line 26-27
Column 5, line 9
Column 5, line 22
Column 7, line 26
Column 8, line 39
Column 13, line 16
Column 14, line 38
Column 15, line 18
Column 16, line 15
Column 16, line 19
Column 16, line 33
Column 19, line 14
Column 19, line 38
Column 19, line 54

Column 4, line 30 -- there should be a space between "africana" and "stem".
Column 8, line 62, the word "Clutia" should be capitalized.
Column 9, line 1, the words "Clutia" and "Dovyalis" both should be capitalized.
Column 9, line 31, the dimensions given should read 3 cm x 2 cm.

This certificate supersedes the Certificate of Correction issued September 15, 2009 and October 6, 2009.

Signed and Sealed this
Eighteenth Day of January, 2011

David J. Kappos
*Director of the United States Patent and Trademark Office*

Column 20, line 12 (Claim 10, line 1) "The herbal pharmaceutical composition of claim 37" should read --The herbal pharmaceutical composition of claim 8--.

Column 20, line 13 (Claim 10, line 2) the word "*non-polar*" should be in plain text, not italics --non-polar--.